(12) United States Patent
Munk

(10) Patent No.: US 7,458,939 B2
(45) Date of Patent: Dec. 2, 2008

(54) PROCEDURE FOR EXTRACTING INFORMATION FROM A HEART SOUND SIGNAL

(75) Inventor: Flemming Munk, Viborg (DK)

(73) Assignee: Bang & Olufsen Medicom A/S, Struer (DK)

( * ) Notice: Subject to any disclaimer, the term of this patent is extended or adjusted under 35 U.S.C. 154(b) by 172 days.

(21) Appl. No.: 10/531,170

(22) PCT Filed: Oct. 9, 2003

(86) PCT No.: PCT/DK03/00680

§ 371 (c)(1),
(2), (4) Date: Apr. 11, 2005

(87) PCT Pub. No.: WO2004/032741

PCT Pub. Date: Apr. 22, 2004

(65) Prior Publication Data

US 2006/0142667 A1    Jun. 29, 2006

(30) Foreign Application Priority Data

Oct. 9, 2002    (DK) ............................... 2002 01521

(51) Int. Cl.
*A61B 5/02* (2006.01)
(52) U.S. Cl. ..................................... 600/528
(58) Field of Classification Search .............. 600/528, 600/508, 586
See application file for complete search history.

(56) References Cited

U.S. PATENT DOCUMENTS 3,318,303 A * 5/1967 Hammacher ................. 600/485
3,581,735 A * 6/1971 Gentner et al. .............. 600/528
4,378,022 A * 3/1983 Suobank et al. ............. 600/528
4,446,873 A * 5/1984 Groch et al. ................. 600/528
4,649,930 A * 3/1987 Groch et al. ................. 600/508
4,967,760 A * 11/1990 Bennett et al. .............. 600/528
5,012,815 A * 5/1991 Bennett et al. .............. 600/528
5,036,857 A * 8/1991 Semmlow et al. ........... 600/528
5,086,776 A * 2/1992 Fowler et al. ............... 600/455
5,685,317 A * 11/1997 Sjostrom .................... 600/528
5,825,895 A * 10/1998 Grasfield et al. ............. 381/67
6,002,777 A * 12/1999 Grasfield et al. ............. 381/67
6,665,564 B2 * 12/2003 Lincoln et al. ................ 607/17
2002/0173826 A1 * 11/2002 Lincoln et al. ................. 607/9

OTHER PUBLICATIONS

A Haghighi-Mood and J N Torry, A Sub-Band Tracking Algorithm for Heart Sound Segmentation, School of Engeineering and Trafford Centre for Medical Research (TCMR), University of Sussex, Brighton, UK, Computers in Cardiology 1995 IEEE, pp. 501-504.

* cited by examiner

*Primary Examiner*—Carl H. Layno
*Assistant Examiner*—Jon-Eric C. Morlaes
(74) *Attorney, Agent, or Firm*—David S. Safran; Roberts Mlotkowski Safran & Cole, P.C.

(57) ABSTRACT

A procedure for extracting features from phonocardiographic signals without the use of synchronizing information from electrocardiographic signals. The features extracted are the timing and value of first and second heart sounds and various combinations of timing and value of signal components constituting heart murmur. Such combinations are directly related to various heart conditions, which are more easily diagnosable by a medically trained person when assisted by the signal extraction. The features are extracted by a novel combination of energy/time relationships for the heart signal and various novel classification schemes.

4 Claims, 5 Drawing Sheets

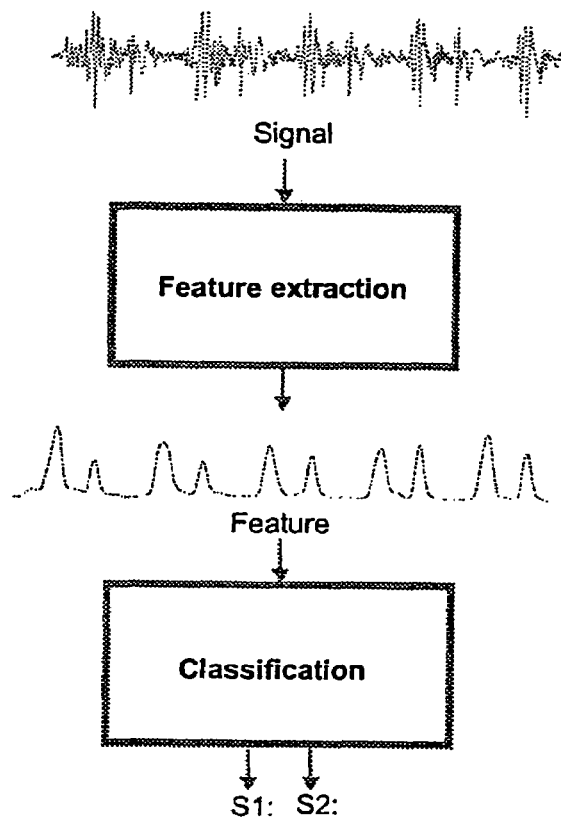
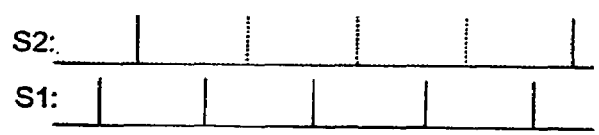
Fig. 2
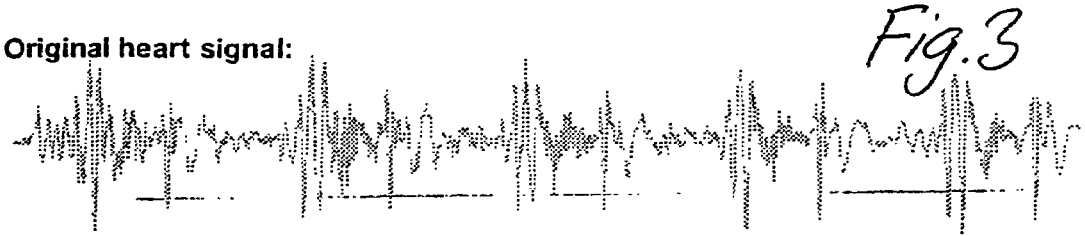
Fig. 3
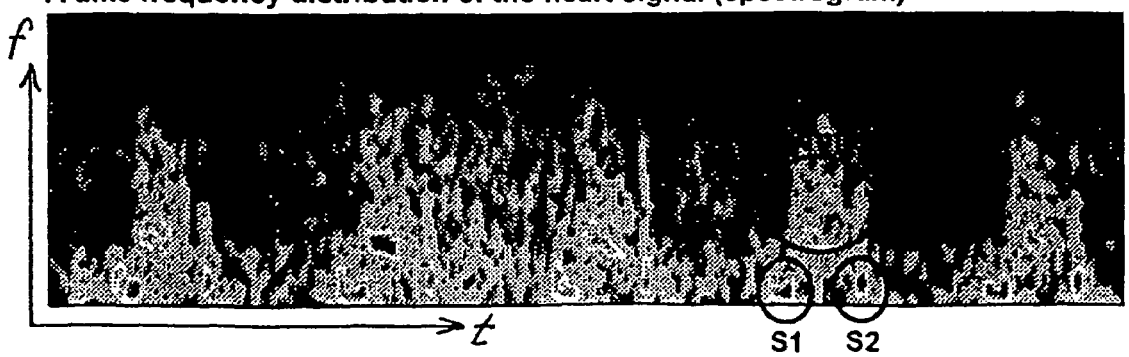

PROCEDURE FOR EXTRACTING INFORMATION FROM A HEART SOUND SIGNAL

BACKGROUND OF THE INVENTION

1. Field of the Invention

The invention relates to a procedure for extracting information from a phonocardiographic signal obtained from a transducer and subjected to signal processing in order to aid evaluation and diagnosis of heart conditions. The invention furthermore relates to techniques forming part of such extraction and apparatus to perform such feature extraction as well as coding the features to aid the ability to distinguish between related features.

2. Description of Related Art

Signals obtained by means of a transducer are phonocardiographic representations of sounds traditionally listened to by means of a stethoscope. Training in auscultation takes a long time and requires an aptitude for recognising and classifying aural cues, frequently in a noisy environment. 20-30 different conditions may need to be differentiated, and within each, the severity evaluated. Furthermore, there may be combinations among these. These factors contribute to explaining why not all physicians perform equally well when diagnosing heart conditions, and why it may be time-consuming.

The so-called first (S1) and second (S2) heart sound are very important markers in the assessment of a heart sound signal. These sounds are directly related to the functioning of the heart valves, in that S1 is caused by the closure of the atrioventricular valves and contraction of the ventricles and S2 is caused by the closure of the aortic and pulmonary valves.

It has been tried to use further signals derived from ECG signals to determine the points in time during which to expect specific heart sounds, such as U.S. Pat. No. 5,685,317, and as described in Haghighi-Mood, A. et al. "A sub-band energy tracking algorithm for heart sound segmentation", In: Computers in Cardiology 1995, Vienna, Austria, 10-13 Sep. 1995, pp. 501-504, which latter is model-based (AR). The extra complication of using ECG in addition to phonocardiographic signals is not generally desirable.

A number of patents relate to the extraction of the S1 and S2 signals, such as U.S. Pat. No. 6,048,319, which concerns the measurement of the time interval between the S1 and S2 signals in relation to the heart rate in order to determine the degree of coronary artery disease. The measurement is based on peak detection and autocorrelation and it may be considered a relatively slow process.

In order to determine the occurrence of the first and second heart sounds a wavelet analysis and re-synthesis and various time occurrence manipulations are used in Huiying, L. et al. "A heart sound segmentation algorithm using wavelet decomposition and reconstruction", ENGINEERING IN MEDICINE AND BIOLOGY SOCIETY, 1997. PROCEEDINGS OF THE 19TH ANNUAL INTERNATIONAL CONFERENCE OF THE IEEE, Chicago, Ill., USA, 30 Oct.-2 Nov. 1997, Vol. 4, pp. 1630-1633. It is described as being a good basis for further analysis of heart sound signals.

In PCT Application Publication WO 02/096293 A1 a complex procedure is described, comprising the use of wavelets, calculating the signal's Shannon's energy, calculating the area of each of a number of energy envelopes, and performing cluster analysis. The latter is needed to identify the S1 and S2 signals, but it is a complicated procedure, and the output of the complex procedure is a number of diagnoses, including murmur.

A different category of signals related to various heart conditions is generally known as murmurs. The known procedures of isolating and categorizing murmurs are generally dependent on the simultaneous recording of electrocardiographic data, such as U.S. Pat. Nos. 5,957,866 and 6,050,950 and this complicates the practical use of auscultation techniques considerably.

The above solutions are very complex and rely on techniques that are equivalent to a long averaging time. According to the invention a method has been derived which is more precise and obtains a faster result. This is obtained by a sequence of steps, comprising an optional adaptive noise reduction, detection of S1 and S2, e.g. by means of the feature extraction procedure mentioned above, enhancement of the signal by elimination of the S1 and S2 contributions, performing spectral analysis and feature enhancement in order to obtain the energy content present in areas of a time-frequency representation delimited by frequency band times time interval in the form of energy distributions, classifying the energy distributions according to pre-defined criteria, and comparing the energy distributions to a catalogue of distributions related to known medical conditions and extracting information by comparing the enhanced signal to stored time functions.

SUMMARY OF THE INVENTION

According to the present invention the detection of S1 and S2 is obtained by performing the steps of feature extraction and classification based on the energy distribution over time in a feature time function. The feature extraction is performed by the steps of bandpass filtering, followed by instantaneous power and lowpass filtering. This generates a series of signal peaks or "hills", each relating to either an S1 or an S2, and a signal classification step determines which "hill" is to be regarded as either an S1 or an S2, whereby a systole is correctly identified.

The correct placement in time of S1 and S2 permits the energy relating to these sounds to be eliminated in the signal processing, and the resulting sound (including murmurs, etc.) is a useful starting signal for further analysis, because it increases the dynamic range of the remaining signal. It also permits presenting the remaining signal to the ears with a superposition of correctly placed but "neutral" S1 and S2 contributions as mere time markers, but without any signal that the listener needs to process in the listening process.

Diagnostic classification and evaluation is obtained by identifying specific features in order to extract characteristic patterns which are compared to a library of patterns typical of various kinds of heart disorder, and the closeness of the measured signal to these patterns.

Enhanced appreciation and identification of the heart sound features is obtained by "placing" the extracted features in a synthetic acoustic environment relying on supplying different signals to the ears of a listener by means of headphones. This is obtained by means of so-called Head Related Transfer Functions, or HRTF.

A specific procedure of the invention is characteristic in that first and second heart sounds are detected and placed correctly on a time axis by performing the steps of feature extraction and classification based on the energy distribution over time in a feature time function by the steps of bandpass filtering, followed by instantaneous power and lowpass filtering of the original phonocardiographic signal.

An embodiment of the invention is particular in that it comprises the steps of extracting the first and second heart sounds by classification according to energy levels, eliminating the contribution of the said first and second heart sounds from the signal, performing spectral analysis and feature enhancement in order to obtain the energy content present in areas of a time-frequency representation delimited by frequency band times time interval in the form of energy distributions, classifying the energy distributions according to pre-defined criteria comparing the energy distributions to a catalogue of distributions related to known medical conditions.

A further advantageous embodiment of the invention for extracting murmur information is particular in that it comprises the steps of obtaining a digital representation of heart sound for a predetermined number of seconds, identifying the time of occurrence of the first and second heart sounds in each cycle, windowing the parts of heart sounds falling between the first and second heart sounds, and second and first heart sounds, respectively; decomposition of the signals into a predetermined first number nil of frequency bands, each band being decomposed into a predetermined second number n2 of time-slices, obtaining a systole (SP) and a diastole (DP) power vector consisting of the sum of n1 powers measured in each of the n2 time slices, for each combination of a frequency band and a time slice, the power values from the different systoles being compared, and the median value being chosen to be the standard value for a power vector, obtaining a systole (SMF) and a diastole (DMF) mean frequency vector by weighting the power value for each of n1 frequency bands with the mean frequency of the corresponding band, summing the results and dividing the sum by the corresponding element in the respective systole or diastole power vector, while using the time of occurrence of the intensity vectors of the various classes for classifying the time distribution of murmurs.

A further embodiment of the invention is particular in that it comprises a step preceding the step of obtaining systole and diastole murmur intensity vectors SI and DI, namely refining the windowing by setting the values of SP, DP, SMF, and DMF of the first or last elements equal to the second or last-but-one values, respectively, if the values of the first or last elements of the corresponding vectors fulfil predetermined deviation criteria.

A further embodiment of the invention is particular in that still further steps are included, namely subjecting the signal to double differentiation before decomposition, obtaining a systole (SI) and diastole (DI) murmur intensity vector, respectively, by taking the logarithm of the corresponding SP and DP vectors, classifying the obtained logarithmic vectors into murmur intensity classes, and comparing the energy distributions to a catalogue of distributions related to known medical conditions.

An apparatus for performing the basic procedure of the invention is particular in that it comprises analog-to-digital means for converting a heart sound signal into sampled data, means for extracting the first and second heart sounds by classification according to energy levels, means for eliminating the contribution of the said first and second heart sounds from the signal, means for performing spectral analysis, means for performing feature enhancement, and multiplication means for obtaining the energy content present in areas of a time-frequency representation delimited by frequency band multiplied by time interval in the form of energy distributions means for classifying the energy distributions according to pre-defined criteria, and comparator means for comparing the energy distributions to a catalogue of distributions related to known medical conditions.

An embodiment of the inventive apparatus is particular in that signal processing means are used to produce a spatial sound distribution based on frequency, a low frequency band being delivered to a first earpiece of a headphone and a high frequency band being delivered to a second earpiece of said headphone, the frequency bands containing first and second heart sounds and murmur sounds respectively.

A further embodiment of the apparatus is particular in that said signal processing means produce a temporal sound distribution, sound signals being first delivered to a first earpiece of the headphone and then being delivered to a second earpiece of the headphone.

A further embodiment of the apparatus is particular in that said signal processing means comprise at least one Wiener filter.

The invention will be more fully described in the following with reference to the drawing, in which

BRIEF DESCRIPTION OF THE DRAWINGS

FIG. 2 shows the structure providing the first analysis of the heart signal, FIG. 3 shows an original heart signal and its corresponding spectrogram.

DETAILED DESCRIPTION OF THE INVENTION

Figure 1:
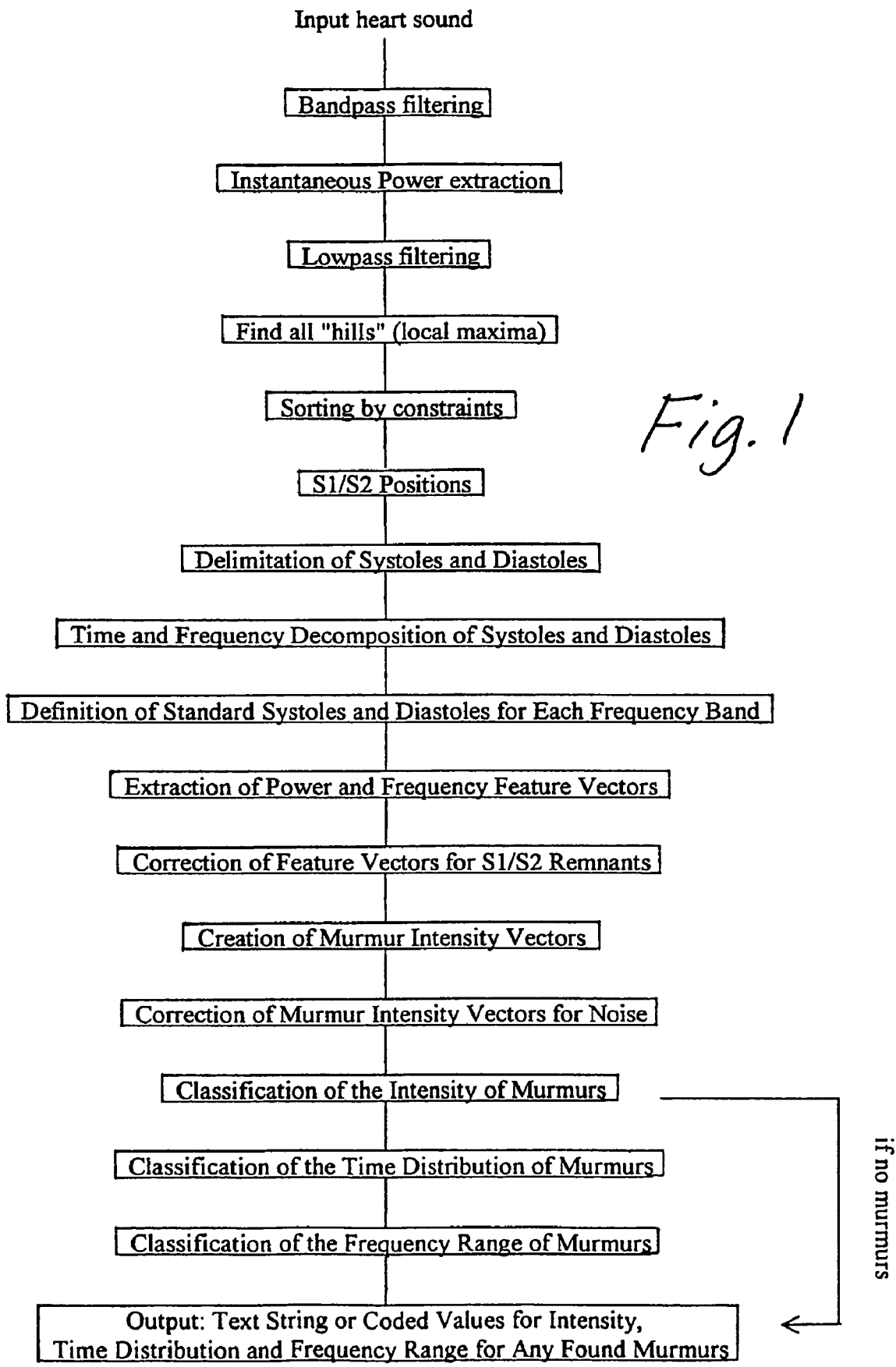
FIG. 1 shows a functional block diagram of the complete information extraction process according to the invention.
Figure 4:
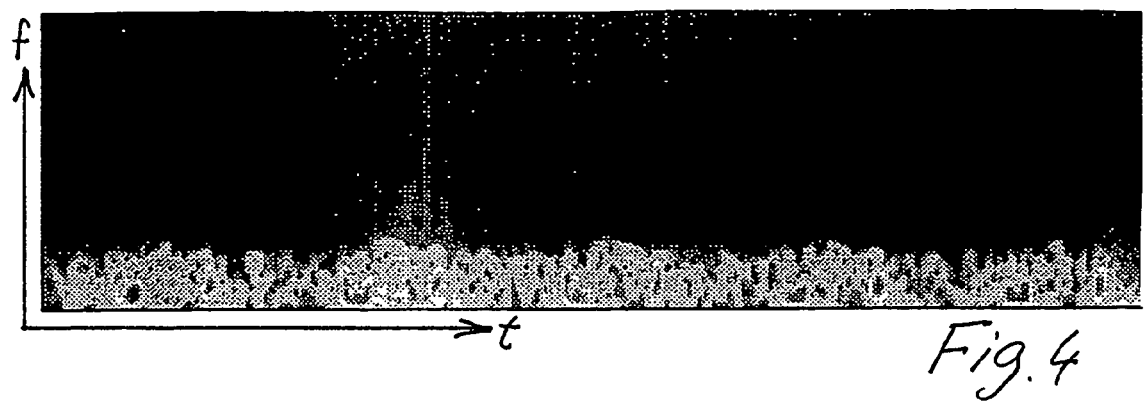
FIG. 4 shows the spectrogram of a bandpass filtered heart signal.

In FIG. 1 is seen a functional block diagram of an embodiment of the procedure and sub-procedures according to the invention. The following description relates to a practical example of an embodiment according to the invention.

Example 1

The input for the procedure consists of 8 seconds of heart sound signal, sampled at a rate of 1000 Hz and read into a digital register subsequent to A/D conversion. The procedure is described with reference to modern digital technology, however in principle the various classification and sorting of time intervals and levels may be performed by analogue means on DC voltages and traditional gates.

The detector for S1 and S2 essentially consists of two separate processes, a feature extraction part and a classification part. The purpose of the feature extraction is to transform the input signal to a domain, in which the respective location in time of S1 and S2 is more distinct than in the original signal. The classification part determines the precise location of S1 and S2 and correctly identifies them as such.

In FIG. 2 is demonstrated how murmurs may be observed in the spectrogram of a time function of an original heart sound. The spectrogram is obtained by Fast Fourier Transform. The first and second heart sounds S1 and S2 have only a low-frequency content compared to the broad-band nature of the murmurs, and for this reason the signal is band-pass filtered by convolution of the original signal with the impulse response function of a bandpass filter. The corresponding spectrogram is shown in FIG. 3, in which peaks of higher energy are visible but not clearly identifiable. In order to obtain a time function of the occurrence of these higher energies, the time marginal distribution of the spectrogram is performed according to Eq. (1):

$$f(t) = \frac{1}{2\pi} \int \left| \int \bar{x}(\tau) g(t-\tau) e^{-j\omega\tau} d\tau \right|^2 d\omega$$

Figure 5:
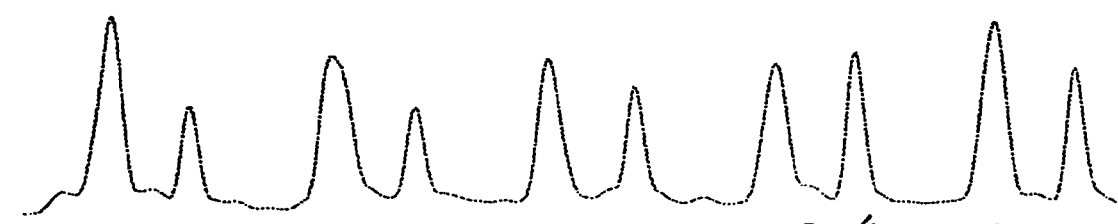
FIG. 5 shows the result of a time marginal distribution of the energy.
Figure 6:
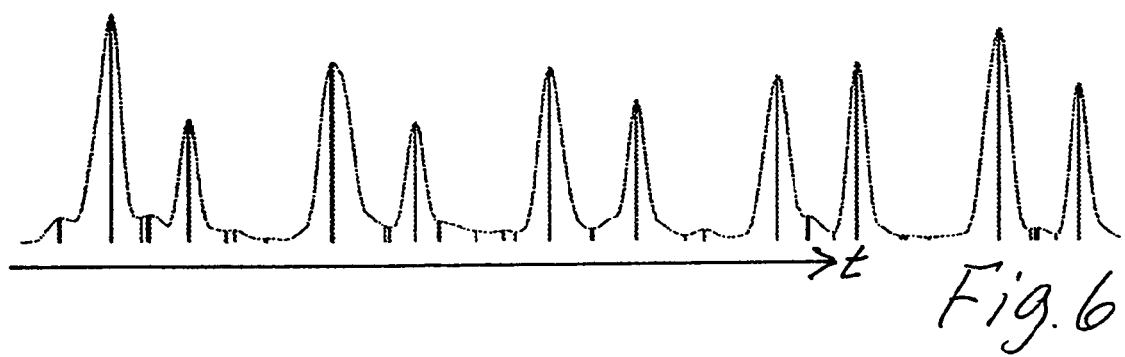
FIG. 6 shows the identification of large and small "hills" in the feature.

Hereby a "final feature" is obtained as a time function as shown in FIG. 5. In essence, this time function is obtained by bandpass filtering, instantaneous power extraction and low-pass filtering. It is now clear that the "final feature" displays a "hill" every time an S1 or S2 occurs in the heart signal.

As the magnitudes of the "hills" corresponding to S1 and S2 are comparable, it is necessary to distinguish between them by applying classification rules. First all "hills" in the "final feature" must be identified. This is obtained for all samples of the time function which fulfil the following criteria:

feature(k−1)<feature (k) and feature(k)>feature (k+1).

The next step is to construct a table of possible systoles. A systole is a pair of "hills" (S1 and S2) constrained by the time distance between the "hills". The time distance must fall within the following limits:

230 ms<T<500 ms for human hearts.

The final sequences of systoles is determined by finding the sequence of systoles in the table having maximum energy that fulfil the following constraints:

systole time deviation<18%
time between systoles (diastole)>0.9 times systole time
amplitude deviation of S1<500%
amplitude deviation of S2<500% in the case of overlapping systoles, the systole with maximum energy must be selected.

Figure 7:
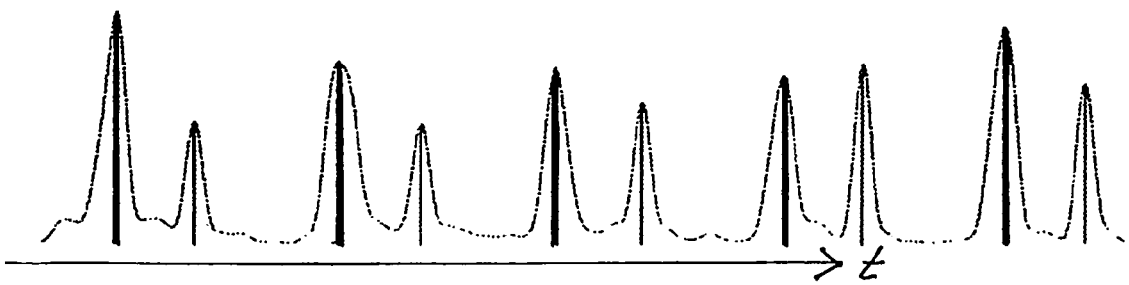
FIG. 7 shows the identification of S1 and S2 irrespective of relative power, FIGS. 8($a$) and 8($b$) are representations of the Wiener scenario as applied to synthesis and analysis, respectively, of filters for right and left ears for stereo headphones according to the invention.

The result of the identification is displayed in FIG. 7, in which a fat black line to the top of a "hill" indicates the time position of a first heart sound S1 and a thin black line a second heart sound S2.

With the time positions of the first (S1) and second (S2) heart sounds correctly detected in the signal (given as sample numbers, corresponding to positions measured in milliseconds) it is now possible to evaluate the much weaker sounds, the heart murmurs. In the following, these detected time positions will be referred to as S1 markers and S2 markers, respectively. Reference is again made to FIG. 1.

Delimitation of Systoles and Diastoles.

Only the systole and diastole parts of the heart sound signal are used for the murmur detection. All periods, beginning 50 milliseconds after an S1 marker and ending 50 milliseconds before the immediately following S2 marker, are defined as systoles.

Correspondingly, all periods, beginning 50 milliseconds after an S2 marker and ending 50 milliseconds before the immediately following S1 marker, are defined as diastoles. This is a primitive but efficient manner of eliminating the influence of the very energetic first and second heart sounds.

At a later stage in the performance of the procedure some corrections are made (vide below), but it may be more advantageous to perform the elimination using more refined approaches at this early stage in the procedure.

Time and Frequency Decomposition of Systoles and Diastoles.

The sound energy content in the sound signal is calculated by means of a spectrogram based on the Discrete Fourier Transform (DFT) using a vector length which is a power of 2, such as 16. In order to be able to classify murmurs regarding frequency contents and time distribution, each systole and diastole is decomposed into 14 frequency bands and 10 time slices, the two lowest frequency bands being discarded. The 14 frequency bands cover the frequency range from 62.5 Hz to 500 Hz, each having a width of 31.25 Hz.

Before the calculation of the spectrogram, the sound signal is differentiated twice (corresponding to a second order high-pass filtration) in order to take into account the frequency characteristics of the human hearing, being more sensitive to higher than lower frequencies within the frequency range in question.

It is considered that a parallel bank of band pass filters will perform faster in the present environment.

The 10 time slices for a given systole or diastole all have the same width, corresponding to 1/10 of the total length of the systole/diastole.

The combination of frequency bands and time slices creates a 14×10 matrix for each systole/diastole. For each element in these matrices, the energy content is divided by the width of the relevant time slice, thus yielding matrices containing the heart sound power (energy per time) for the 140 time/frequency elements of each systole/diastole.

Definition of Standard Systoles and Diastoles for Each Frequency Band.

The matrices for each systole are combined to a single 14×10 systole (S) matrix by median filtration:

For each combination of a frequency range and a time slice, the power values from the different systoles are compared, and the median value is chosen to be the standard value. This is an efficient way of obtaining a stable value. Thus, for each of the 14 frequency bands (rows in the matrix), 10 standard power values combine to a standard systole.

The diastole matrices are combined to a D matrix in the same way.

Extraction of Power and Frequency Feature Vectors.

A systole power (SP) vector with 10 elements is constructed by summing the 14 standard power values for each of the 10 time slices. Thus, the SP vector consists of the column sums for the S matrix.

A diastole power vector (DP) is constructed in the same way.

A systole mean frequency (SMF) vector (also with 10 elements) is calculated by weighting the power value for each frequency band with the mean frequency of the corresponding band, summing the 14 results, and dividing the sum with the corresponding element in the SP vector.

Correspondingly, a diastole mean frequency (DMF) vector is calculated.

Correction of Feature Vectors for S1/S2 Remnants.

Due to the very simple definition of systoles and diastoles, the first and/or last tenths of some of the systoles and diastoles may be "contaminated" with parts of S1 or S2. Typically, this is manifested by larger values of the first/last elements in SP/DP and lower values of the corresponding elements in SMF/DMF, because of the high power and the relatively low frequencies of S1 and S2 compared to the murmurs in systoles and diastoles.

Therefore, the beginning and end of the SP, SMF, DP, and DMF vectors are examined and corrected if necessary in dependence of the following relationships:

If SMF(2)−SMF(1)>2*|SMF(3)−SMF(2)| or

SP(1)−SP(2)>2*|SP(2)−SP(3)|,

SP(1)==SP(2) and SMF(L)==SMF(2).

If SMF(9)−SMF(10)>2*|SMF(8)−SMF(9)| or

SP(10)−SP(9)>2*|SP(9)−SP(8)|,

SP(10)==SP(9) and SMF(10)==SMF(9).

Corresponding examinations and corrections are performed for DP and DMF. Creation of Murmur Intensity Vectors.

The elements in a systole intensity (SI) vector is created from the elements in the SP vector in the following way using absolute values:

| | |
|---|---|
| log10(SP(x)) ≦ −1.25 | SI(x) = 0 |
| −1.25 < log10(SP(x)) ≦ −0.80 | SI(x) = 1 |
| −0.80 < log10(SP(x)) ≦ −0.35 | SI(x) = 2 |
| −0.35 < log10(SP(x)) ≦ +0.10 | SI(x) = 3 |
| +0.10 < log10(SP(x)) ≦ +0.55 | SI(x) = 4 |
| +0.55 < log10(SP(x)) ≦ +1.00 | SI(x) = 5 |
| +1.00 < log10(SP(x)) | SI(x) = 6 |

A diastole intensity (DI) vector is constructed in the same way.

It may be relevant to use values relative to e.g. the intensity of S1 and/or S2, in which case the logarithmic conversion may use other limits than given above.

Correction of Murmur Intentity Vectors for Noise.

In order to correct for transient noise signals, the following corrections are performed:

SI(1) is set to 0, if SI(2) is 0

SI(10) is set to 0, if SI(9) is 0

If any element in SI is more than 1 larger than both of its neighbours, the element is set to be equal to the highest of the neighbours.

Similar corrections are performed for DI.

Classification of the Intensity of Murmurs.

The intensities of any systolic and/or diastolic murmur is defined as being the maximum value of SI and/or DI, resp.

If the maximum values are both 0, the heart sound is classified as containing no murmurs.

Classification of the Time Distribution of Murmurs.

If at least one of the maximum values found is larger than 0, the systolic and/or diastolic murmurs are classified according to the profiles of SI and DI, resp.

Any systolic murmur is classified within the first class in the list below whose description matches the content of SI:

Systolic ejection murmurs: The values in SI are increasing to a certain point and decreasing after that point.
Steps that are neither in- or decreasing are allowed within the increasing as well as the decreasing part of the vector.
Early systolic murmurs: The last five values in SI are all 0.
Early-mid systolic murmurs: The last three values in SI are all 0.
Late systolic murmurs: The first five values in SI are all 0.
Mid-late systolic murmurs: The first three values in SI are all 0.
Pansystolic murmurs: The SI vector does not match any of the above descriptions.

Any diastolic murmur is classified within the first class in the list below whose description matches the content of DI:
Decreasing diastolic murmurs: The values in DI are decreasing, but never increasing.
Steps that are neither in- or decreasing are allowed.
Diastolic murmurs with pre-systolic accentuation: DI(9) >DI(8) and DI(10)>DI(9).
Uniform diastolic murmurs: The DI vector does not match any of the above descriptions.

Classification of the Frequency Range of Murmurs.

Systolic and diastolic murmur frequencies are classified according to the frequency band containing the largest power value in the tenth(s) of the systole/diastole corresponding to the found maximum values of SI/DI.

If the largest power value is found in one of the two lowest frequency bands (containing frequencies below 125 Hz), the murmur is classified as a low-frequency murmur.

If the largest power value is found in one of the eight highest frequency bands (containing frequencies above 250 Hz), the murmur is classified as a high-frequency murmur.

If the none of the above is the case, the murmur is classified as a medium-frequency murmur.

Use of the Murmur Detection Output.

The output from the procedure is either a string describing the found murmur(s) or three values for each found murmur coding for the intensity, the time distribution and the frequency range of the murmur(s). The values may either be used for classification or form the coordinates in a murmur representation It will be noted that in the above description of a specific embodiment that apparently arbitrary steps were introduced of double differentiation (second-order highpass filtering) and of applying a logarithmic function in order to obtain intensity values. These steps have a psychoacoustic foundation related to the hearing of the auscultating person. It is obvious that the classification may well proceed without these steps, however it has been determined in practical use that the classifications obtained by applying these steps are commensurate with observations made by trained medical staff, and that the results thereby obtained are much more directly applicable to the auscultated phenomena at hand. In this way the medical professional will be much further aided than by mere reading and comparing sets of three values.

Example 2

The extraction of features may be used in an enhanced manner by creating a synthetic spatial environment for two ears to listen to via headphones. The ability to distinguish more clearly between several simultaneously occurring phenomena has been used by jet airplane pilots to increase separation when listening to several communication channels simultaneously. The use of special filters for these purposes is known and research has been conducted to determine the filter effect of the head (characterized as Head related Transfer Functions, HRTFs) with regard to sound from two microphones based on the distance and source; see, HRTF Measurements of a KEMAR Dummy-Head Microphone, Bill Gardner and Keith Martin, MIT Media Lab, (HTTP://sound- .media.mit.edu/KEMAR/hrtfdoc.txt, Aug. 8, 2000). However, to date, no known attempt has been made to use this ability in connection with features extracted from a heart signal and presented as index markers simultaneously with the heart signal itself so as to present different features to each of the physician's ears.

Figure 8A:
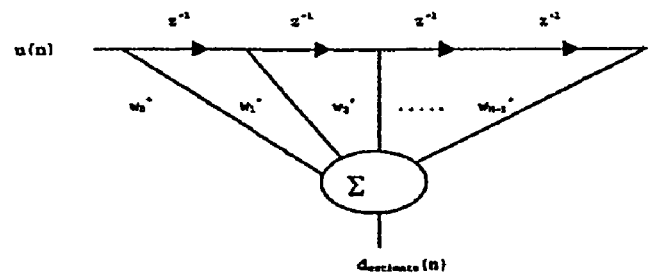
Figure 8B:
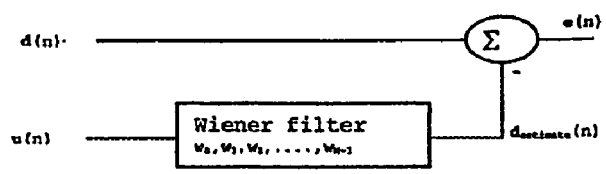

FIGS. 8(a) & 8(b) show one manner in which filters can be used to spatially distribute the sounds delivered to the physician's ears to reflect the angular difference between sounds received by the left and right ears. In particular, either the signal to both ears can be filtered or the original signal can be preserved and sent to one ear. To do so, it is necessary to synthesize the difference at each angle, and this can be done by applying the known Wiener scenario, by which an estimate of the optimal filter coefficients for a specified FIR filter can be arrived at.

In FIGS. 8(a) & 8(b), $d_{estimate}(n)$ designates the impulse response signal $z^{-1}$ to be synthesized for the ear farthest away from the source, and $u(n)$ designates the impulse response for the other ear, which by proper filtering should mimic $d_{estimate}(n)$. By means of a least mean square algorithm, the coefficients w are adjusted to minimize the error signal $e(n)$. These special filters, one for each angle, are used to arbitrarily place a sound spatially when listening via a stereo headset, the original sound being presented to one ear and a filtered version to the other ear.

Figure 9:
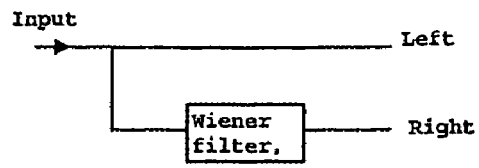
FIGS. 9 & 10 are representations, respectively, of a one and a two band approach to the application of the Wiener scenario to the stereo headphones according to the invention.
Figure 10:
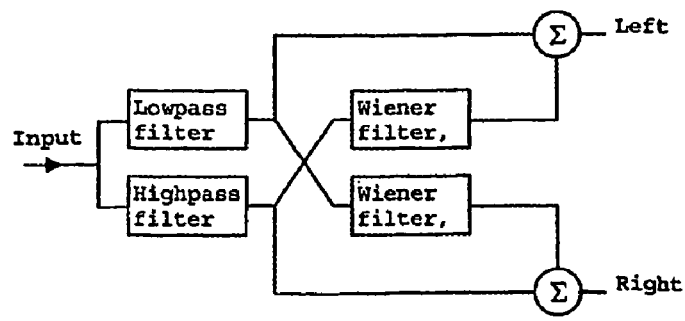

The listening experience can also be expanded by creation of a synthetic listening space in which low frequency sounds, such as heart beats with the enhancements described in Example 1, are perceived as coming from, e.g., the left side while high frequency sounds, such as heart murmurs, from the right side. Similarly, earlier phenomena could be made to appear on, e.g., the left side and subsequent phenomena on the right so that, with a repetitive sequence, there would be a repetition of sounds moving from left to right. In these manners, separating and distinguishing of features is facilitated. FIGS. 9 & 10 represent one band and two band scenarios, respectively, for achieving these effects. In FIG. 9, the input sound passes through to the left ear, while the signal to the right ear is processed in one of the above manners. In FIG. 10, the input sounds are separated and independently processed en route to each ear.

Figure 11:
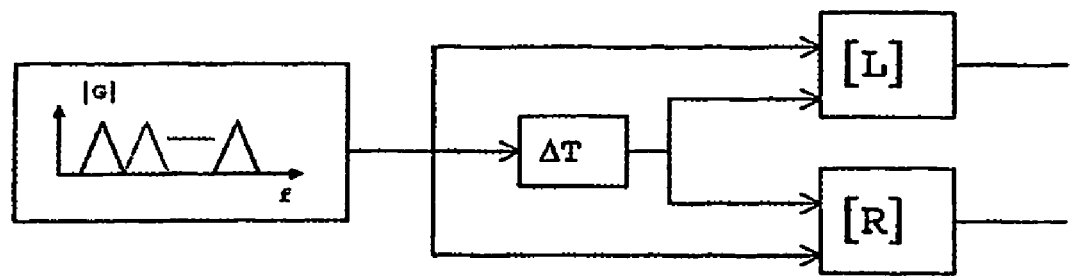
FIG. 11 is a representation of an alternative manner of presenting heart sounds to right and left ears with the stereo headphones according to the invention.

FIG. 11 shows an arrangement for transformation of heart sounds from frequency distribution to a spatial distribution. The sound signal is first divided into a number of frequency bands by normal filters or orthogonal filters, orthogonal filters preventing redundancy, which ensures energy preservation. The output from each filter has a direct path and a delayed path to the matrix circuits for the left and right channels. In the matrices, a weighted sum of the input signals is formed in such a way that the lowest to highest frequency bands are perceived as being spatially distributed from left to right, when played back via a stereo speaker system or preferably via a stereo headset. In this way, an alternative presentation can be offered which adds a new dimension to the sound, which apparently enhances the perceived frequency resolution, and by that, the ability to recognize murmurs etc.

Figure 12:
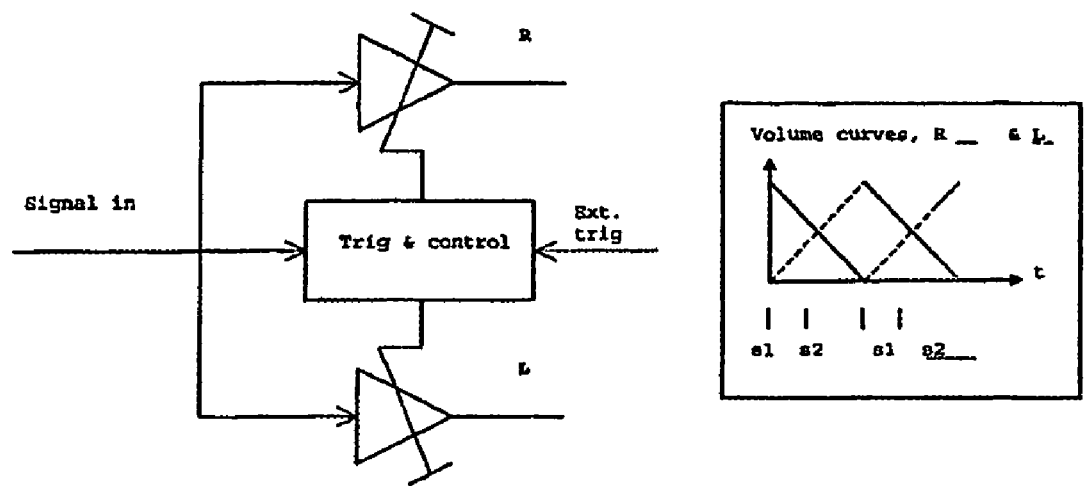
FIG. 12 is a modified embodiment for spatially distributing heart sounds.

FIG. 12, on the other hand, shows an arrangement for the transformation heart sounds from a temporal distribution to a spatial distribution. In this embodiment, the spatial location of the sound follows the temporal location in the heart cycle, from a first heart sound to the next first heart sound, s1 to s1. This means that the systole, s1 to s2, is located on the left side and the diastole, s2 to s1, on the right side. It is like the balance is automatically adjusted with time triggered by a signal derived from the input signal itself. In this way, physicians are offered an alternative presentation which is meant to help locate murmurs in the heart cycle, mainly systolic or mainly diastolic.

It will be understood that once the signal has been converted to digital representation of data, its manipulation may take place in dedicated processors, RISC processors, or general purpose computers, the outcome of the manipulation being solely dependent on the instructions performed on the data under the control of the program written for the processor in order to obtain the function. The physical location of the data at any one instant (i.e. in varying degrees of processing) may or may not be related to a particular block in the block diagram, but the representation of the invention in the form of interconnected functional blocks provides the skilled person with sufficient information to obtain the advantages of the invention.

The foregoing description of the specific embodiments will so fully reveal the general nature of the present invention that others skilled in the art can, by applying current knowledge, readily modify or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

The invention claimed is:

1. A procedure used for extracting murmur information, characterised in that it comprises the following steps:

obtaining a digital representation of heart sound for a predetermined number of seconds, identifying the time of occurrence of the first and second heart sounds in each cycle, windowing the parts of heart sounds falling between the first and second heart sounds, and second and first heart sounds, respectively decomposition of the signals into a predetermined first number n1 of frequency bands, each band being decomposed into a predetermined second number n2 of time-slices obtaining a systole (SP) and a diastole (DP) power vector consisting of the sum of n1 powers measured in each of the n2 time slices for each combination of a frequency band and a time slice, the power values from the different systoles are compared, and the median value is chosen to be the standard value for a power vector obtaining a systole (SMF) and a diastole (DMF) mean frequency vector by weighting the power value for each of n1 frequency bands with the mean frequency of the corresponding band, summing the results and dividing the sum by the corresponding element in the respective systole or diastole power vector while using the time of occurrence of the intensity vectors of the various classes for classifying the time distribution of murmurs.

2. A procedure for extracting murmur information according to claim 1, characterised in that a step preceding the step of obtaining systole and diastole murmur intensity vectors SI and DI consists of refining the windowing by setting the values of SP, DP, SMF, and DMF of the first or last elements equal to the second or last-but-one values, respectively, if the values of the first or last elements of the corresponding vectors fulfil predetermined deviation criteria.

3. A procedure according to claim 1, characterised in that further steps are included in the procedure, comprising subjecting the signal to double differentiation before decomposition obtaining a systole (SI) and diastole (DI) murmur intensity vector, respectively, by taking the logarithm of the corresponding SP and DP vectors, classifying the obtained logarithmic vectors into murmur intensity classes comparing the energy distributions to a catalogue of distributions related to known medical conditions.

4. An apparatus for performing the procedure of extracting information from a phonocardiographic signals obtained from a transducer and subjected to signal processing including identification of characteristic signal components, comprising the steps of:

detecting first and second heart sounds and placing them correctly on a time axis by performing the steps of:

extracting the first and second heart sounds by classification according to energy levels, then performing instantaneous power and lowpass filtering of the original phonocardiographic signal by performing spectral analysis and feature enhancement to obtain the energy content present in areas of a time-frequency representation delimited by frequency band time intervals in the form of energy distributions, classifying the energy distributions according to pre-defined criteria, comparing the energy distributions to a catalogue of distributions related to known medical conditions, and outputting values for any medical conditions found;

wherein signal processing means are used to produce a spatial sound distribution based on frequency, a low frequency band being delivered to a first earpiece of a headphone and a high frequency band being delivered to a second earpiece of said headphone, the frequency bands containing first and second heart sounds and murmur sounds respectively; and wherein said signal processing means comprise at least one Wiener filter.

\* \* \* \* \*